US011346770B2

(12) United States Patent
Viegas et al.

(10) Patent No.: US 11,346,770 B2
(45) Date of Patent: May 31, 2022

(54) OPTICAL FIBER SENSOR FOR SALINITY AND TEMPERATURE MEASUREMENT

(71) Applicant: Khalifa University of Science and Technology, Abu Dhabi (AE)

(72) Inventors: Jaime Viegas, Abu Dhabi (AE); Raquel Flores, Abu Dhabi (AE); Ricardo Janeiro, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 0 days.

(21) Appl. No.: 17/043,368

(22) PCT Filed: Mar. 28, 2019

(86) PCT No.: PCT/IB2019/052535
§ 371 (c)(1),
(2) Date: Sep. 29, 2020

(87) PCT Pub. No.: WO2019/186448
PCT Pub. Date: Oct. 3, 2019

(65) Prior Publication Data
US 2021/0018431 A1   Jan. 21, 2021

Related U.S. Application Data

(60) Provisional application No. 62/650,031, filed on Mar. 29, 2018.

(51) Int. Cl.
*G01B 9/02*   (2006.01)
*G01N 21/25*   (2006.01)
(Continued)

(52) U.S. Cl.
CPC ........... *G01N 21/255* (2013.01); *G01K 11/32* (2013.01); *G01N 21/31* (2013.01); *G01N 33/18* (2013.01); *G01N 2201/088* (2013.01)

(58) Field of Classification Search
CPC ........... G01D 5/35383; G01D 5/35303; G01D 5/353; G01H 9/004; G01B 9/02
(Continued)

(56) References Cited

U.S. PATENT DOCUMENTS

2001/0040681 A1 * 11/2001 Paiam ................ G02B 6/29358
356/480
2002/0094157 A1 *  7/2002 Xie .................... G02B 6/29395
385/27

FOREIGN PATENT DOCUMENTS

CN      1374529 A    10/2002
CN    102073104 B     7/2012
(Continued)

OTHER PUBLICATIONS

Search Report and Written Opinion for PCT/IB2019/052535 dated Jul. 26, 2019.
(Continued)

*Primary Examiner* — Md M Rahman
(74) *Attorney, Agent, or Firm* — Billion & Armitage (57) ABSTRACT

A fiber-optic salinity and temperature measurement includes a first Fabry-Perot interferometer and a second Fabry-Perot interferometer. Each of the Fabry-Perot interferometers includes a first optical fiber fusion spliced to a second optical fiber such that a relatively large cavity is formed between the fibers. The relatively large cavity forms the measurement chamber for each Fabry-Perot interferometer. The input port on each of the Fabry-Perot interferometers is coupled to an optical splitter such that a single optical signal input is provided to each Fabry-Perot interferometer. The output port on each of the Fabry-Perot interferometers is coupled to an optical combiner that combines the interference signal received from each of the Fabry-Perot interferometers. An optical signal analyzer coupled to an output port of the
(Continued)

optical combiner determines the salinity and temperature of a sample material in the large cavity of the second Fabry-Perot interferometer.

11 Claims, 9 Drawing Sheets

(51) Int. Cl.
*G01K 11/32* (2021.01)
*G01N 21/31* (2006.01)
*G01N 33/18* (2006.01)

(58) Field of Classification Search
USPC .......................................................... 356/478
See application file for complete search history.

(56) References Cited

FOREIGN PATENT DOCUMENTS

| CN | 106289504 A | 1/2017 |
| CN | 106442340 A | 2/2017 |
| CN | 106932026 A | 7/2017 |

OTHER PUBLICATIONS

Bai, et al., "Ultra-Weak Fiber Bragg Grating Sensing Network Coated with Sensitive Material for Multi-Parameter Measurements", Sensors 2017, 17, 1509, 10 pages.

Guzman-Sepulveda, "Fiber Optic Sensor for High-Sensitivity Salinity Measurement", IEEE Photonics Technology Letters, vol. 25, No. 23, Dec. 1, 2013, 2323-2326.

Luo, et al., "In-Fiber Optic Salinity Sensing: A Potential Application for Offshore Concrete Structure Protection", Sensors 2017, 17, 962, 10 pages.

Nguyen, et al., "Three-Wave Fiber Fabry-Pérot Interferometer for Simultaneous Measurement of Temperature and Water Salinity of Seawater", IEEE Photonics Technology Letters, vol. 23, No. 7, Apr. 1, 2011.

Pereira, et al., "Fiber Bragg grating sensing system for simultaneous measurement of salinity and temperature", Opt. Eng. 43(2) 299-304 (Feb. 2004).

Sharma, et al., "On the Application of Different Bimetallic Alloy Nanoparticle Combinations in Fiber Optic Surface Plasmon Resonance Salinity Sensor and Its Performance Optimization Against Thermal Effects", Journal of Nanoscience and Nanotechnology vol. 10, 3145-3154, 2010.

\* cited by examiner

OPTICAL FIBER SENSOR FOR SALINITY AND TEMPERATURE MEASUREMENT

TECHNICAL FIELD

The present disclosure relates to sensors, more specifically to combination salinity and temperature sensors.

BACKGROUND

Salinity and temperature measurements are basic indicators of the health of a marine ecosystem. Fiber Bragg gratings have enjoyed widespread use for the simultaneous measurement of temperature and salinity. Such devices typically include etched fibers cladded along a fiber body. Such fibers may be formed or deposited using one or more methods such as chemical etching or mechanical polishing. The interaction between the evanescent field and the medium surrounding the body causes a Bragg wavelength shift that provides information indicative of the salinity and temperature of the surrounding medium. However such sensors have a relatively low sensitivity due to the dependence on the relatively weak evanescent field. Another weakness of such sensors is their physical fragility when the cladding is removed to expose the sensing element to the surrounding environment.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

Although the following Detailed Description will proceed with reference being made to illustrative embodiments, many alternatives, modifications and variations thereof will be apparent to those skilled in the art.

DETAILED DESCRIPTION

The systems and methods described herein provide salinity and temperature measurements using two Fabry-Perot interferometers, a first Fabry-Perot interferometer provides a reference, the second Fabry-Perot interferometer provides the sensing element. Each of the two Fabry-Perot interferometers includes a sensing cavity formed by fusion splicing a single-mode optical fiber to a graded-index optical fiber. The working principle is based on a change in refractive index of a sample within the sensing cavity. Changes in refractive index change the resonant wavelength of the Fabry-Perot interferometer. In embodiments, any number of Fabry-Perot interferometers may be cascaded in series along the length of an optical fiber, with each interrogated using a different frequency that is independently demodulated to provide a distributed sensing network.

The systems and methods described herein provide a Fabry-Perot interferometer that includes a cavity fabricated in two steps: first, by etching the tip of a graded-index fiber using a hydrofluoric acid gel to create a relatively small cavity on the tip of the graded-index fiber; and second, by fusion splicing the etched tip of the graded-index fiber to a cleaved single-mode fiber. Using defined splicing parameters, the relatively small cavity crated by the hydrofluoric acid etching expands during the splicing process to create a relatively large cavity that acts as a Fabry-Perot interferometer due to the low reflectivity of the glass fiber interfaces that form the two sides of the large chamber. Radial access channels to the relatively large cavity may be milled into the Fabry-Perot interferometer, for example using a focused-ion beam.

The systems and methods described herein may use any broadband optical test source to interrogate the Fabry-Perot sensor and an optical spectral analyzer to receive the optical signal from the Fabry-Perot interferometer. For example, the Fabry-Perot interferometer may be interrogated using a broadband test source having an output of about 1550 nanometers (nm). A sample liquid (e.g., saline water) having different salt concentrations is introduced to the sensing cavity of the Fabry-Perot interferometer. Each salt concentration has a different refractive index that induces a different shift in the resonant wavelength of the Fabry-Perot interferometer. The systems and methods described herein provide an output optical signal that is the sum of the reference and sensing cavities. The salinity of the sample is determined by quantifying the shift in output spectrum. The Vernier effect magnifies the sensitivity of the combined reference and sensing cavities compared to Fabry-Perot interferometers using only a sensing element alone. Beneficially, the systems and methods described herein provide a Fabry-Perot interferometer having a simple structure that is easier and simpler to fabricate, is more compact, and demonstrates a greater sensitivity than a traditional fiber-Bragg grating.

A fiber-optic salinity and temperature sensor is provided. The salinity and temperature sensor may include: a first Fabry-Perot interferometer comprising a reference cell formed between a first single-mode optical fiber and a coaxially aligned first graded-index fiber; a second Fabry-Perot interferometer that includes a measurement cell formed between a second single-mode optical fiber and a coaxially aligned second graded-index fiber; an optical splitter having a first output port optically coupled to the first single-mode optical fiber and a second output port optically coupled to the second single-mode optical fiber; and an optical combiner having a first input port optically coupled to the first graded-index fiber and a second input port optically coupled to the second graded-index fiber.

A salinity and temperature measurement system is provided. The system may include: an optical source; an optical spectral analyzer; and at least one fiber-optic salinity and temperature sensor, the at least one fiber-optic salinity and temperature sensor comprising: a first Fabry-Perot interferometer comprising a reference cell formed between a first single-mode optical fiber and a coaxially aligned first graded-index fiber; a second Fabry-Perot interferometer that includes a measurement cell formed between a second single-mode optical fiber and a coaxially aligned second graded-index fiber; an optical splitter having an input port optically coupled to the broadband optical source, a first output port optically coupled to the first single-mode optical fiber and a second output port optically coupled to the second single-mode optical fiber; and an optical combiner having a first input port optically coupled to the first graded-index fiber, a second input port optically coupled to the second graded-index fiber, and an output port optically coupled to the optical spectral analyzer.

A method for fabricating a fiber-optic salinity and temperature sensor. The method may include: optically coupling an input port of a first Fabry-Perot interferometer to a first output port of an optical splitter; optically coupling an output port of the first Fabry-Perot interferometer to a first input port of an optical combiner; optically coupling an input port of a second Fabry-Perot interferometer to a second output port of the optical splitter; optically coupling an output port of the second Fabry-Perot interferometer to a second input port of the optical combiner; forming each of the first Fabry-Perot interferometer and the second Fabry-Perot interferometer by: etching an end of a graded-index fiber to create a small cavity on the end of the graded-index fiber, wherein the small cavity forms at least a portion of a first surface of a chamber in the respective Fabry-Perot interferometer; coaxially aligning an end of a single-mode fiber with the small cavity formed on the end of the graded-index fiber, wherein the end of the single-mode fiber forms a second reflective surface of the chamber in the respective Fabry-Perot interferometer; fusion splicing the end of the single-mode fiber to the small cavity formed on the end of the graded-index fiber to form a large cavity in the respective Fabry-Perot interferometer; and milling an access channel to the large cavity in the second Fabry-Perot interferometer.

A method for measuring salinity and temperature is provided. The method may include: receiving a broadband optical signal at an input port of an optical splitter; providing the broadband optical signal from a first output port of the optical splitter to a first Fabry-Perot interferometer; providing the broadband optical signal from a second output port of the optical splitter to an input port of a second Fabry-Perot interferometer; wherein both the first Fabry-Perot interferometer and the second Fabry-Perot interferometer include a cavity formed between a single-mode optical fiber and a coaxially aligned first graded-index fiber; generating, by the first Fabry-Perot interferometer, a first optical output signal; generating, by the second Fabry-Perot interferometer, a second optical output signal; receiving at a first input port of an optical combiner, the first optical output signal; receiving at a second input port of an optical combiner, the second optical output signal; combining, by the optical combiner, the first optical output signal and the second optical output signal; generating, by the optical combiner, a combined optical signal that includes information indicative of a salinity and a temperature of a sample introduced to the measurement Fabry-Perot interferometer.

A multipoint salinity and temperature measurement system is provided. The system may include: an optical source to generate an output signal that includes a plurality of frequency bands; a plurality of fiber-optic salinity and temperature sensors disposed serially along a fiber optic cable coupled to the optical source; each of the plurality of fiber-optic salinity and temperature sensors to operate at a respective one of the plurality of frequency bands; each of the fiber-optic salinity and temperature sensors; and each of the fiber-optic salinity and temperature sensors including: a first Fabry-Perot interferometer comprising a reference cell formed between a first single-mode optical fiber and a coaxially aligned first graded-index fiber; a second Fabry-Perot interferometer that includes a measurement cell formed between a second single-mode optical fiber and a coaxially aligned second graded-index fiber; an optical splitter having an input port optically coupled to the broadband optical source, a first output port optically coupled to the first single-mode optical fiber and a second output port optically coupled to the second single-mode optical fiber; and an optical combiner having a first input optically coupled to the first graded-index fiber, a second input optically coupled to the second graded-index fiber, and an output optically coupled to the optical spectral analyzer; and an optical spectral analyzer coupled to the fiber optic cable, the optical spectral analyzer to demodulate each of the plurality of frequency bands and generate an output indicative of a temperature and a salinity corresponding to each of the plurality of fiber-optic salinity and temperature sensors.

As used herein, the term "longitudinal axis" refers to an axis substantially perpendicular to the radius of the respective optical fiber. Thus, as used herein, the longitudinal axis may be considered to run along the length of the optical fiber.

Although the following disclosure references a cavity formed between a single-mode fiber and a graded-index fiber for clarity and conciseness, those of ordinary skill in the art will readily appreciate that either or both the single-mode fiber and the graded-index fiber may be substituted with any currently available or future developed optical fiber. Such embodiments should be considered as falling within the scope of this disclosure. For example, using the systems and methods described herein, a Fabry-Perot interferometer may be formed using two single-mode optical fibers; two graded-index optical fibers; two multi-mode optical fibers; or combinations thereof.

Figure 1A:
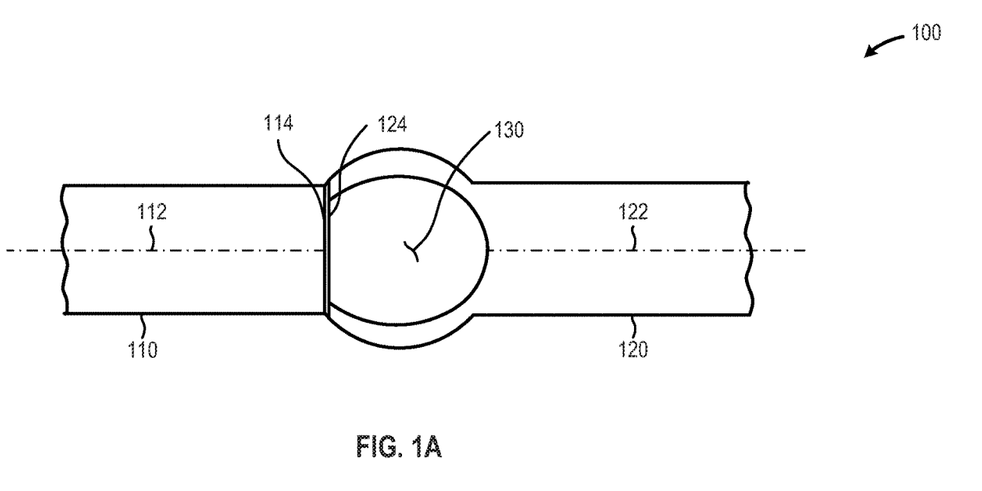
FIG. 1A is a partial cross-sectional elevation of an illustrative Fabry-Perot interferometer that includes a single-mode fiber and graded-index fiber that includes a relatively small cavity formed in the end of the fiber are coaxially aligned preparatory to fusion splicing the single-mode fiber to the graded-index fiber, in accordance with at least one embodiment described herein.
Figure 1B:
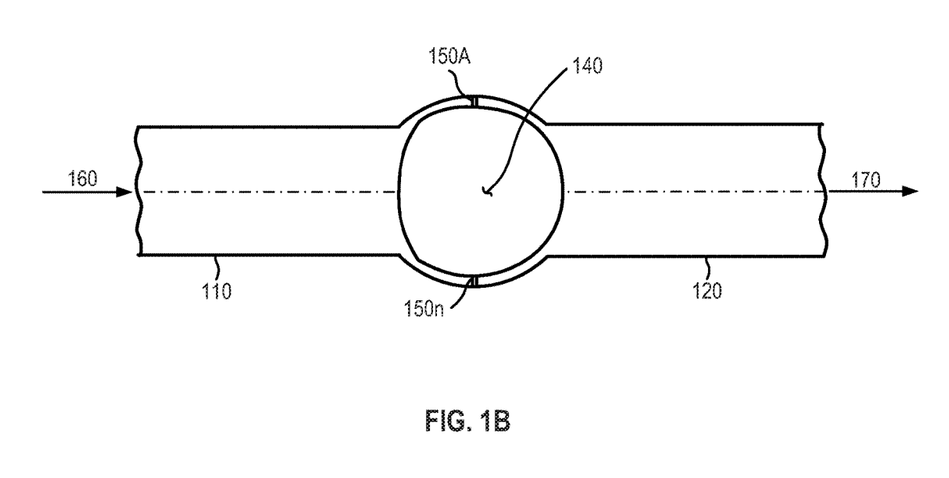
FIG. 1B is a partial cross-sectional elevation of the illustrative Fabry-Perot interferometer depicted in FIG. 1A after fusion splicing the single-mode fiber and the graded-index fiber to form a relatively large cavity, in accordance with at least one embodiment described herein.

FIG. 1A is a partial cross-sectional elevation of an illustrative Fabry-Perot interferometer 100A that includes a single-mode fiber 110 and graded-index fiber 120 that includes a relatively small cavity 130 formed in the end of the fiber are coaxially aligned preparatory to fusion splicing the single-mode fiber 110 to the graded-index fiber 120, in accordance with at least one embodiment described herein. FIG. 1B is a partial cross-sectional elevation of the illustrative Fabry-Perot interferometer 100 depicted in FIG. 1 A after fusion splicing the single-mode fiber 110 and the graded-index fiber 120 to form a relatively large cavity 140, in accordance with at least one embodiment described herein. One or more access channels 150A-150n may be formed radially about the relatively large cavity 140. As depicted in FIG. 1B, an source provides electromagnetic energy 160 to the Fabry-Perot interferometer 100 via the single-mode fiber 110. The electromagnetic output signal 170 generated by the Fabry-Perot interferometer 100 exits via the graded-index fiber 120.

Turning first to FIG. 1A, a single-mode fiber 110 having a longitudinal axis 112 is cut, or severed to form an end 114. A graded-index fiber 120 having a longitudinal axis 122 is also cut or severed to form an end 124. A relatively small cavity 130 is formed on the end surface of the graded-index fiber 120. The ends of the single-mode fiber 110 and the graded-index fiber 120 are positioned preparatory to fusion splicing such that the longitudinal axis 112 of the single-mode fiber 110 and the longitudinal axis 122 of the graded-index fiber 120 coaxially align.

In embodiments, the single-mode fiber 110 may include any currently available or future developed single-mode fiber. In embodiments, the single-mode fiber 110 may include a core with a higher refractive index than the cladding surrounding the core. The single-mode fiber may include a buffer or similar protective coating at least partially surrounding the cladding. In embodiments, the single-mode fiber 110 may include a core having a diameter of less than: about 50 micrometers (µm); about 30 µm; about 20 µm; or about 10 µm. For example, the single-mode fiber 110 may have a core diameter of about 9 µm. In embodiments, the single-mode fiber 110 may have an overall diameter of less than: about 200 micrometers (µm); about 150 µm; or about 100 µm. For example, the single-mode fiber 110 may have an outside diameter of about 125 µm. In implementations, the single-mode fiber 110 may optionally include an optical trench that at least partially surrounds the core. In embodiments, the single-mode fiber 110 may include optical fibers compliant with the latest version of one or more of the following industry specifications: International Telecommunication Union (ITU) G.652; ITU G.653; ITU G.654; ITU G.655; or ITU G.657.

In embodiments, the graded-index fiber 120 may include any currently available or future developed graded-index fiber. In embodiments, the graded-index fiber 120 may include a core having a parabolic index profile and a higher refractive index than the cladding surrounding the core. The graded-index fiber 120 uses variations within the composition of the glass core to compensate for different modal path lengths. In embodiments, the graded-index fiber 120 may include a core having a diameter of less than: about 100 micrometers (µm); about 70 µm; about 60 µm; or about 50 µm. For example, the graded-index fiber 120 may have a core diameter of 50 µm or 62.5 µm. In embodiments, the graded-index fiber 120 may have an overall diameter of less than: about 200 micrometers ( µm); about 150 µm; or about 100 µm. For example, the graded-index fiber 120 may have an outside diameter of about 125 µm. In some implementations, the graded-index fiber 120 may optionally include an optical trench that at least partially surrounds the core. In embodiments, the graded-index fiber 120 may include optical fibers compliant with the latest version of the International Telecommunication Union (ITU) 651.1 industry standard.

The relatively small cavity 130 may be formed on the end 124 of the graded-index fiber 120 using any chemical and/or mechanical method or system. In embodiments, the relatively small cavity 130 may be formed using an acidic material capable of etching or removing glass from the core and/or cladding of the graded-index fiber 120. For example, the relatively small cavity 130 may be formed using a hydrofluoric acid gel or similar material capable of chemically attacking the core and/or cladding of the graded-index fiber 120. In one example, a 9.8% hydrofluoric acid gel may be used to create the relatively small cavity 130 on the end 124 of the graded-index fiber 120. In embodiments, the relatively small cavity 130 may have an axial depth (i.e., a depth measured along the longitudinal axis 122 of the graded-index fiber 120) of greater than: about 10 micrometers ( µm); about 20 µm; about 40 µm; about 50 µm; about 100 µm; or about 150 µm. For example, the relatively small cavity may have a depth of between 100 µm and 125 µm. In embodiments, the relatively small cavity 130 may have a diameter of less than: about 110 µm; about 90 µm; about 70 µm; or about 50 µm.

Referring now to FIG. 1B, the single-mode fiber 110 and the graded-index fiber 120 have been fusion spliced to create a unitary fiber. The fusion splicing process transforms the relatively small cavity 130 to a relatively large cavity 140. In embodiments, a number of access channels 150A-150n may fluidly couple the relatively large cavity 140 to the external environment about the Fabry-Perot interferometer 100. In embodiments, the fusion splicing parameters may be based on the physical parameters of the single-mode fiber 110, the graded-index fiber 120, the relatively small cavity 130, or combinations thereof. In one example, the fusion splicing parameters may include: a gap of 10 micrometers (µm) to 20 µm; an axial offset of 20 µm to 40 µm; and an arc time of 200 milliseconds (ms) to about 600 ms. In embodiments, the standard electrode current may be 5 mA to 100 mA, for example 15 mA. In embodiments, the fusing arc may be applied for 1 to 10 seconds, for example 3 -6 seconds. In embodiments, trigger voltages of 2,000VDC to 15,000VDC may be applied, for example 10,000VDC. In embodiments, the arc discharge voltage may be 200VAC to about 1,000VAC, for example 500VAC to 600VAC. In embodiments, the arc discharge frequency may be 50 kHz to 500 kHz, for example 100 kHz. In embodiments, the power per splice may be 5 W to 50 W, for example 8 W to 10 W.

Figure 2:
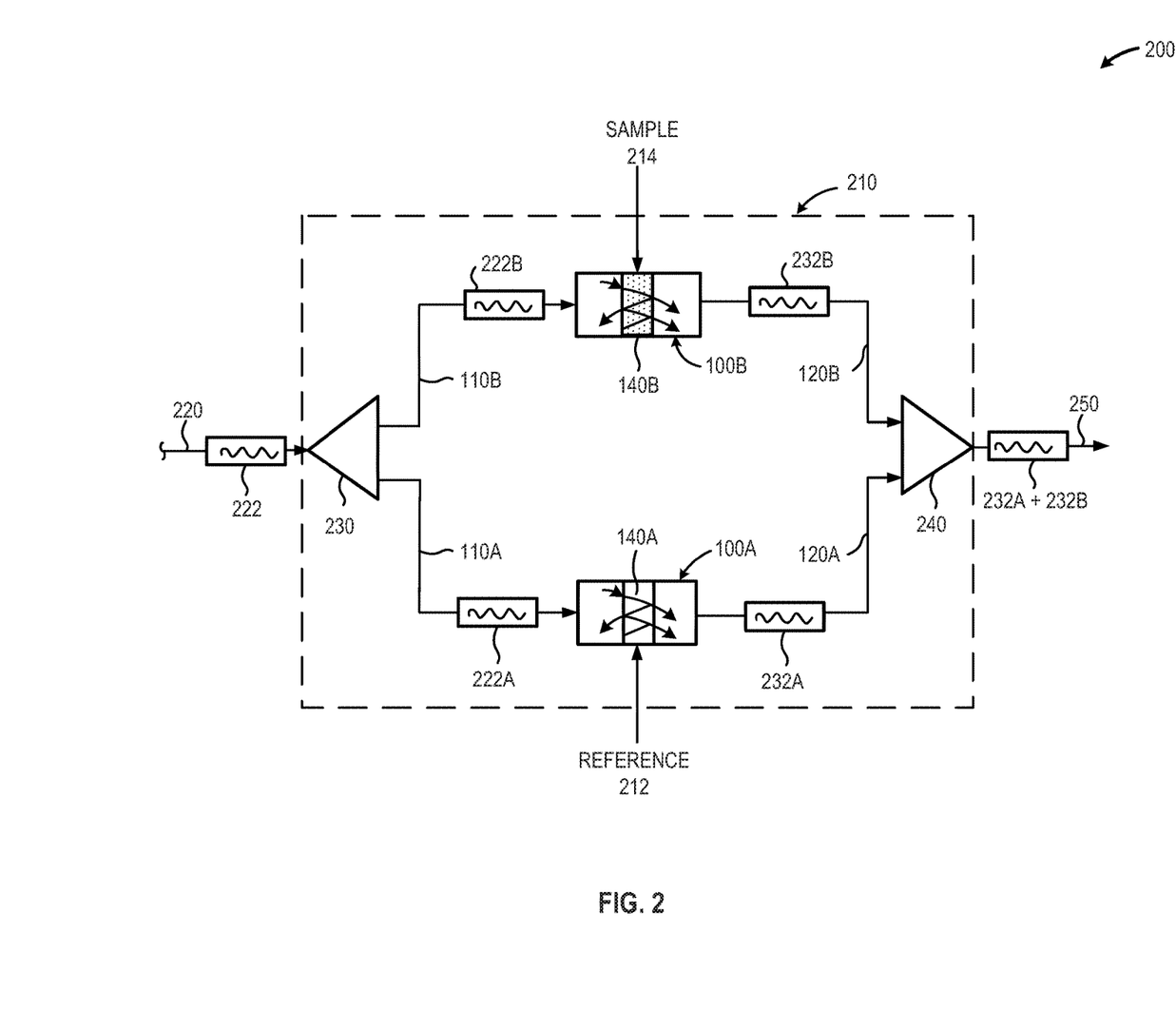
FIG. 2 is a schematic diagram of an illustrative salinity and temperature measurement system that includes a salinity and temperature sensor incorporating a first Fabry-Perot interferometer that receives a reference material and a second Fabry-Perot interferometer that receives a sample material, in accordance with at least one embodiment described herein.

FIG. 2 is a schematic diagram of an illustrative salinity and temperature measurement system 200 that includes a salinity and temperature sensor 210 incorporating a first Fabry-Perot interferometer 110A that receives a reference material 212 and a second Fabry-Perot interferometer 110B that receives a sample material 214, in accordance with at least one embodiment described herein. The salinity and temperature sensor 210 includes an optical signal splitter 230 that receives via an optical fiber 220 coupled to an input port, an optical signal 222. The optical signal splitter 230 provides the optical signal 222 to the first Fabry-Perot interferometer 100A via the single-mode fiber 110A coupled to a first output port. The optical signal splitter 230 also provides the optical signal 222 to the second Fabry-Perot interferometer 100B via the single-mode fiber 110B coupled to a second output port.

The salinity and temperature sensor 210 also includes an optical signal combiner 240 that receives an optical output signal 232A from the first Fabry-Perot interferometer 100A via the graded-index fiber 120A coupled to a first input port. The optical combiner 240 also receives an optical output signal 232B from the second Fabry-Perot interferometer 100B via the graded-index fiber 232B coupled to the second input port. The optical combiner 240 combines the received optical output signals 232A and 232B to produce a combined optical output signal 250 that includes information indicative of the salinity and/or temperature of the sample material introduced to the second Fabry-Perot interferometer 100B. The combined optical output signal 250 may be provided to one or more external devices, such as an optical spectral analyzer, to determine values representative of the salinity and/or temperature of a sample material introduced to or flowing through the second Fabry-Perot interferometer 100B.

The optical splitter 230 includes any number and/or combination of currently available and/or future developed systems and/or devices having at least one input port coupleable to optical fiber 220 and capable of receiving the output signal 222. The optical splitter 230 additionally includes any number and/or combination of currently available and/or future developed systems and/or devices having a first output port coupleable to the first single-mode fiber 110A and a second output port coupleable to the second single-mode fiber 110B. The optical splitter 230 receives the input signal 222 and provides, a first output signal 222A at the first output port. The first optical output signal 222A is provided to the first Fabry-Perot interferometer 100A via the first single-mode fiber 110A coupled to the first output port. The optical splitter 230 also provides, the second output signal 222B at the second output port. The second optical output signal 222B is provided to the second Fabry-Perot interferometer 100B via the second single-mode fiber 110B coupled to the first output port.

In embodiments, the spectral content of the two optical output signals 222A and 222B may be the same. For example, each of the optical output signals 222A and 222B may include all or identical portions of the spectral content of the optical signal 222. In embodiments, the spectral content of the two synchronous optical output signals 222A and 222B may be different. For example, the optical output signal 222A may include a first portion of the spectral content of the optical signal 222 and the optical output signal 222B may include a different, second, portion of the spectral content of the optical signal 222.

The first Fabry-Perot interferometer 100A receives the optical output signal 222A from the optical splitter 230. The first Fabry-Perot interferometer 100A generates a first optical output signal 232A that includes data and/or information representative of an interference pattern caused, at least in part, by the refractive index of the reference material 212 disposed in the large cavity 140 in the first Fabry-Perot interferometer 100A. The reference material 212 may include one or more liquids or one or more gases. For example, the reference material 212 may include air (i.e., a gas mixture containing primarily nitrogen and oxygen with smaller quantities of trace elements). In some implementations, the reference material 212 may be hermetically sealed inside the first Fabry-Perot interferometer 100A.

The second Fabry-Perot interferometer 100B receives the optical output signal 222B from the optical splitter 230. The second Fabry-Perot interferometer 100B generates a second optical output signal 232B that includes data and/or information representative of an interference pattern caused, at least in part, by the refractive index of the sample material 214 introduced to or flowing through the large cavity 140 in the second Fabry-Perot interferometer 100B. The sample material 214 may include one or more liquids or one or more gases. For example, the sample material 214 may include a saline solution having an unknown concentration of one or more salt compounds. In such an embodiment, the second output signal 232B may include an interference pattern that includes information and/or data indicative of a salt concentration in (e.g., the salinity of) the sample material 214 introduced to the second Fabry-Perot interferometer 100B. Additionally, the second output signal 232B may include information and/or data representative of the temperature of the sample material 214 in the second Fabry-Perot interferometer 100B.

The signal combiner 240 receives the first optical output signal 232A from the first Fabry-Perot interferometer 100A via the first graded-index fiber 232A coupled to a first input port and the second output signal 232B from the second Fabry-Perot interferometer 100B via the second graded-index fiber 232B coupled to a second input port. The signal combiner 240 combines the optical output signals 232A and 232B to provide the combined optical output signal 250. The combined optical output signal 250 contains information and/or data representative of one or more properties of the sample material 214 in the second Fabry-Perot interferometer 100B. For example, if the sample material 214 includes a saline solution, the combined optical output signal 250 contains information representative of an interference pattern indicative of the salt concentration in the saline solution sample 214 and indicative of the temperature of the saline solution sample 214.

The optical combiner 240 may include any number and/or combination of currently available and/or future developed systems and/or devices capable of receiving the first output signal 232A from the first Fabry-Perot interferometer 100A and the second output signal 232B from the second Fabry-Perot interferometer 100B. In addition, the optical combiner 230 may include circuitry, systems, or devices capable of combining all or a portion of the first optical output signal 232A with all or a portion of the second optical output signal 232B to provide a combined optical output signal 250 that includes information and/or data (e.g., interference patterns) from each of the received first optical output signal 232A and second optical output signal 232B.

Figure 3:
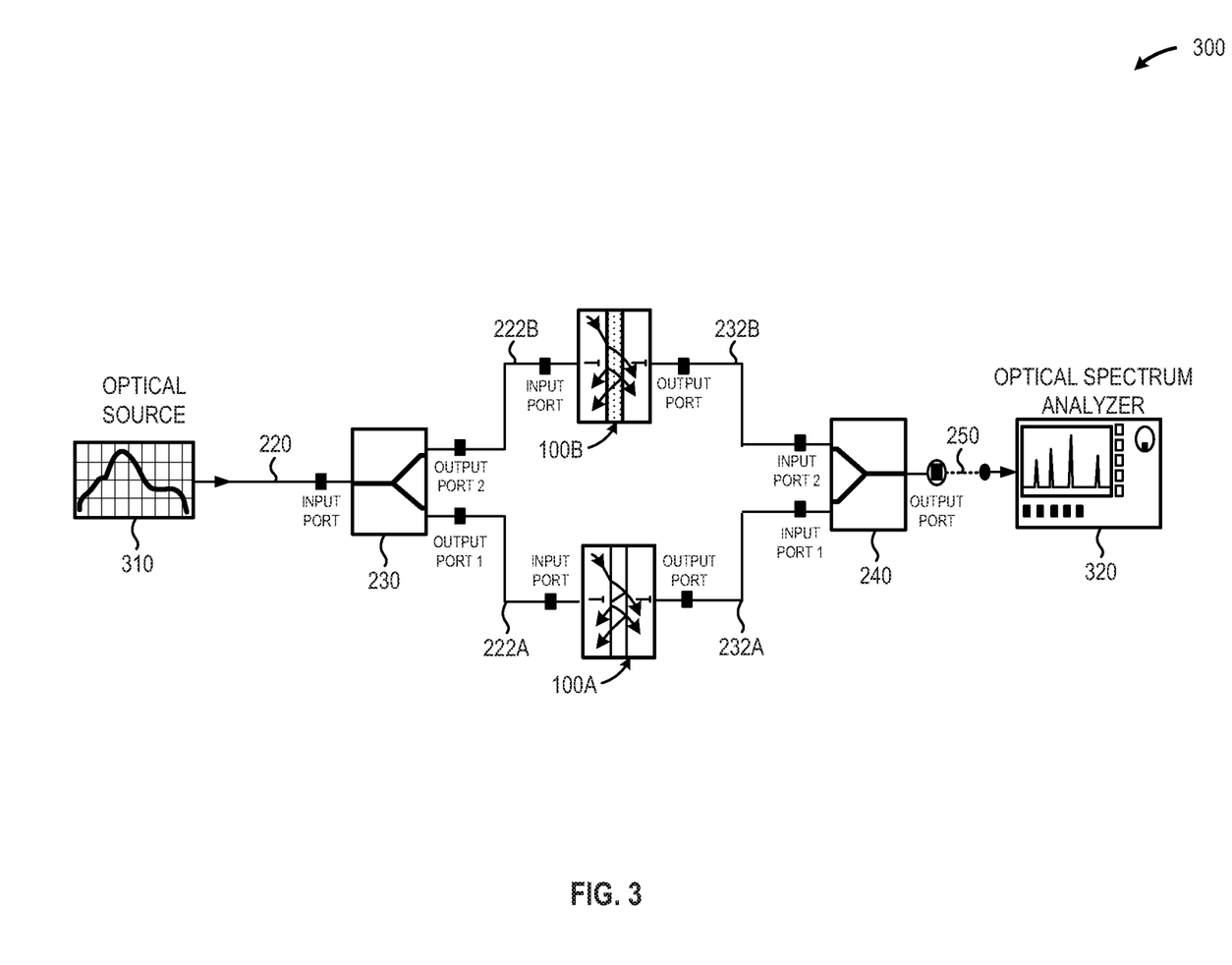
FIG. 3 is a schematic diagram of an illustrative system that includes a broadband optical source operably coupled, via fiber, to the optical splitter and an optical spectral analyzer operably coupled to the optical combiner, in accordance with at least one embodiment described herein.

FIG. 3 is a schematic diagram of an illustrative system 300 that includes an optical source 310 operably coupled, via optical fiber 220, to the optical splitter 230 and an optical spectral analyzer 320 operably coupled to the optical combiner 240, in accordance with at least one embodiment described herein. As depicted in FIG. 3, the optical source 310 provides the output 222 to the optical splitter 230 and the optical spectral analyzer 320 receives the combined optical output signal 250 from the optical combiner 240.

The optical source 310 may include any number and/or combination of systems and/or devices capable of producing an optical signal 222 having a defined spectral content at an output port coupled to the optical fiber 220. In embodiments, the optical source 310 may include one or more circuits, hardware, firmware, or combinations thereof capable of producing a broadband output signal 222. In embodiments, the optical source 310 may include circuits, hardware, firmware, or combinations thereof to produce an optical signal 222 over one or more relatively broad frequency/ wavelength bands. In other embodiments, the optical source 310 may include circuits, hardware, firmware, or combinations thereof to produce an optical signal 222 over one or more relatively narrow frequency/wavelength bands. In other embodiments, the optical source 310 may include circuits, hardware, firmware, or combinations thereof to produce an optical signal 222 at one or more single frequencies/wavelengths. For example, the optical source 310 may include circuits, hardware, firmware, or combinations thereof capable of producing a broadband optical signal 222 at a wavelength of about 1550 nanometers (nm). In embodiments, the optical source 310 may include circuits, hardware, firmware, or combinations thereof to produce an optical output signal 222 that includes any number and/or combination of frequency/wavelength bands.

The optical spectral analyzer 320 may include any number and/or combination of currently available and/or future developed systems and/or devices capable of receiving the combined optical output signal 250 from one or more salinity/temperature sensors 210. The optical spectral analyzer 320 may include circuitry, hardware, firmware, or combinations thereof capable of detecting a shift or difference in the interference patterns provided by the first Fabry-Perot interferometer 100A and the second Fabry-Perot interferometer 100B. The optical spectral analyzer 320 may include circuitry, hardware, firmware, or combinations thereof capable of determining values corresponding to a salinity of a sample material 214 in the second Fabry-Perot interferometer 100B based on the detected shift or difference in the interference patterns provided by the first Fabry-Perot interferometer 100A and the second Fabry-Perot interferometer 100B included in the combined optical output signal 250. In embodiments, the optical spectral analyzer 320 may demodulate a plurality of combined optical output signals 250 each at a different spectral frequency/wavelength or different spectral frequency/wavelength band.

In embodiments, the optical spectral analyzer may be disposed as depicted in FIG. 3 in which the combined optical signal 250 provided by the Fabry-Perot interferometer 210 is in a transmission mode such that the optical source 310 and the optical spectral analyzer 320 are positioned on opposite sides of the Fabry-Perot interferometer 210. Such an arrangement permits the optical spectral analyzer 320 to receive the portion of the combined optical signal 250 transmitted by the Fabry-Perot interferometer 210. However, one of ordinary skill in the relevant arts will readily appreciate that the optical source 310 and the optical spectral analyzer 320 may be disposed on the same side of the Fabry-Perot interferometer 210 such that the portion of the combined optical signal 250 reflected by the Fabry-Perot interferometer 210 provides the input to the optical spectral analyzer 320.

Figure 4:
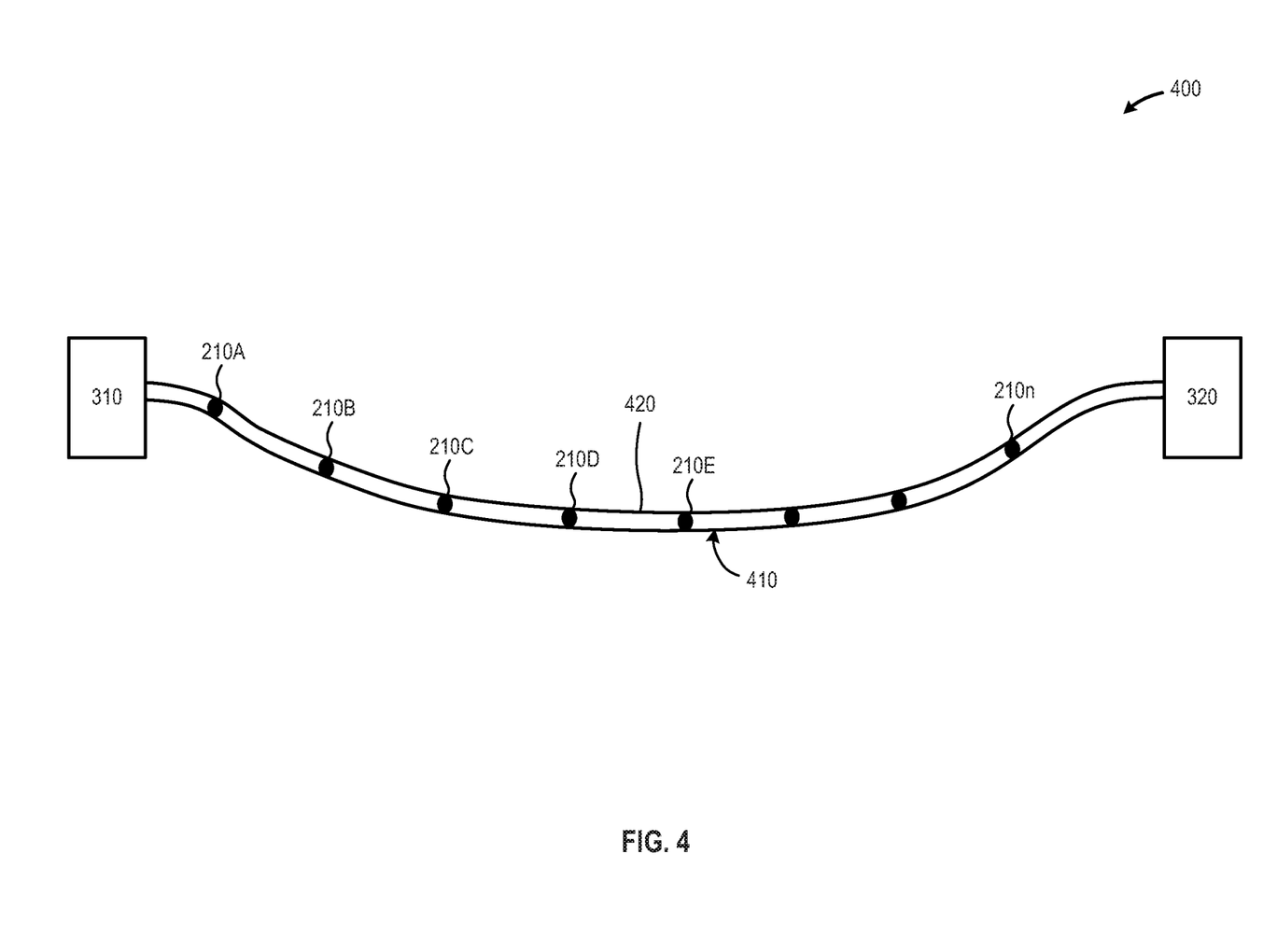
FIG. 4 is a schematic diagram of an illustrative system that includes a sensor array that incorporates a plurality of salinity and temperature sensors disposed along a fiber optic cable, an optical signal generator coupled to the fiber optic cable, and an optical spectral analyzer coupled to the fiber optic cable, in accordance with at least one embodiment described herein.

FIG. 4 is a schematic diagram of an illustrative system 400 that includes a sensor array 410 that incorporates a plurality of salinity and temperature sensors 210A-210$n$ disposed along a fiber optic cable 420, an optical source 310 coupled to the fiber optic cable 420, and an optical spectral analyzer 320 coupled to the fiber optic cable 420, in accordance with at least one embodiment described herein. Although the sensor array 410 is depicted as a one-dimensional (i.e., linear) sensor array, the salinity and temperature sensors 210A-210$n$ may be configured with an appropriate number of optical signal splitters and optical signal combiners to provide two-dimensional and even three-dimensional arrays, all of which should be considered as included in this disclosure.

In embodiments, the optical source 310 generates an optical output signal 222 that includes a plurality of frequency bands. Each frequency band included in the plurality of frequency bands may include an electromagnetic energy contribution at one or more frequencies or across one or more frequency bands. Each of the plurality of salinity and temperature sensors 210A-210$n$ responds to a respective one of the one or more frequency bands to generate a respective combined optical output signal 250A-250$n$ that includes salinity and temperature information and/or data corresponding to the environmental conditions proximate the respective salinity and temperature sensor 210.

The optical spectral analyzer 320 receives the optical output signals 250A-250$n$ from each of the plurality of salinity and temperature sensors 210A-210$n$. The optical spectral analyzer 320 demodulates each of the optical output signals 250A-250$n$ received from each of the salinity and temperature sensors 210A-210$n$. The optical spectral analyzer 320 quantifies the shift in the output spectrum in each of the output signals 250A-250$n$ to determine values representative of a salinity and a temperature proximate each respective one of the salinity and temperature sensors 210A-210$n$ included in the sensor array.

Figure 5A:
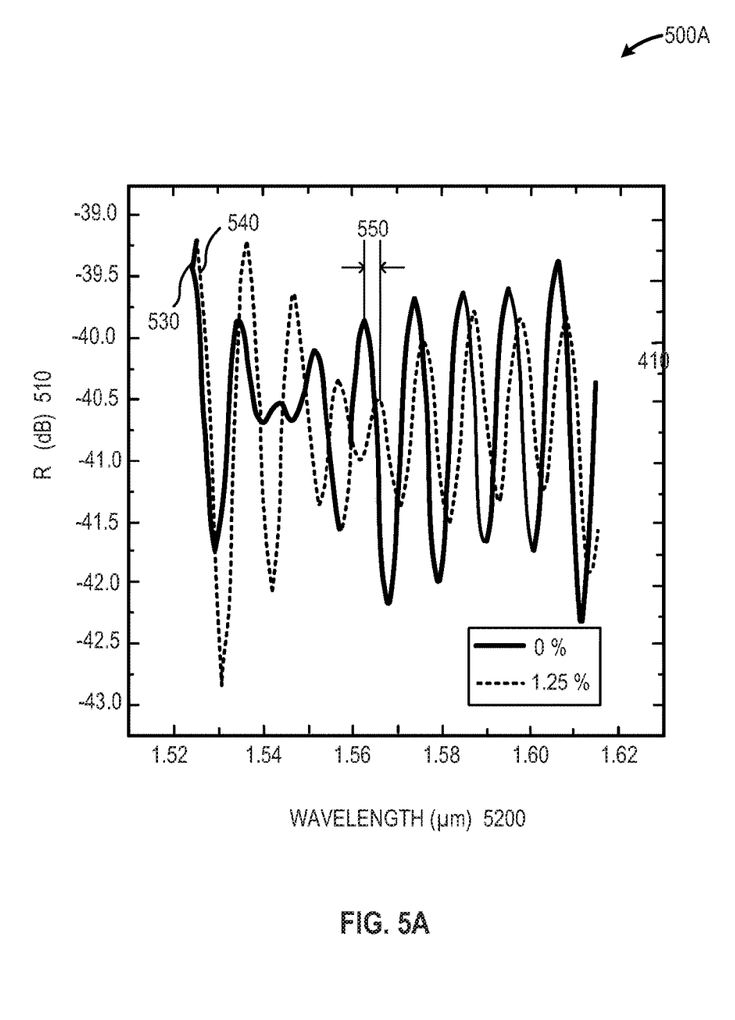
FIG. 5A is a graph in which a first curve represents the optical output spectrum of an illustrative Fabry-Perot interferometer such as depicted in FIG. 3 when placed in pure water (i.e., 0% salt solution), and in which a second curve represents the optical output spectrum of the illustrative Fabry-Perot interferometer when placed in a 1.25% salt solution in accordance with at least one embodiment described herein.
Figure 5B:
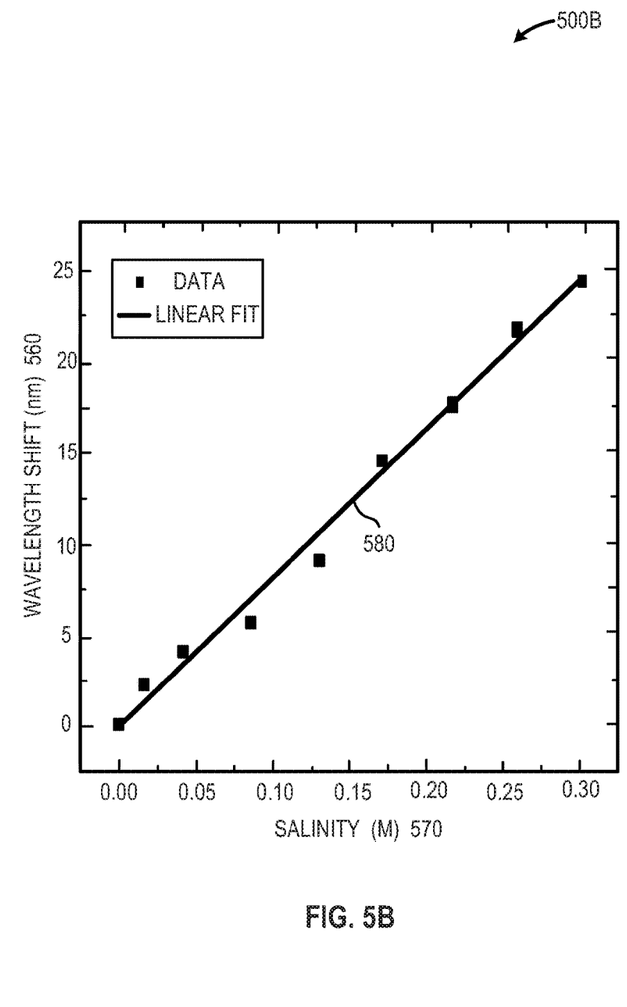
FIG. 5B is a graph that illustrates the salt concentration sensitivity of the illustrative Fabry-Perot interferometer, such as depicted in FIG. 3, as a function of wavelength shift, in accordance with at least one embodiment described herein.

FIG. 5A is a graph 500A in which curve 530 represents the optical output spectrum of an illustrative Fabry-Perot interferometer 300 such as depicted in FIG. 3 when placed in pure water (i.e., 0% salt solution), and in which curve 540 represents the optical output spectrum of the illustrative Fabry-Perot interferometer 300 when placed in a 1.25% salt solution in accordance with at least one embodiment described herein. FIG. 5B is a graph 500B that illustrates the salt concentration sensitivity of the illustrative Fabry-Perot interferometer 300, such as depicted in FIG. 3, as a function of wavelength shift attributable to changes in the refractive index of the liquid in which the Fabry-Perot interferometer 300 is placed, in accordance with at least one embodiment described herein.

Referring first to FIG. 5A, graph 500A depicts relative signal strength 510 (in decibels, dB) as a function of wavelength 520 (in micrometers, μm). Curve 530 represents the signal strength of a Fabry-Perot interferometer 300 (such as described above in reference to FIG. 3) when placed in pure water. Curve 540 depicts the signal strength of the Fabry-Perot interferometer 300 when placed in a 1.25% salt solution. The shift or offset 550 between curve 530 and curve 540 is caused by the difference in the refractive indices of the reference material (pure water, 0% salt) and the sample material (1.25% salt solution). The difference in refractive indices provides an indication of the salt concentration of the solution in which the Fabry-Perot interferometer 300 is placed. The optical spectrum analyzer 320 determines the salinity of the solution based on the measured difference in refractive indices as manifested in the offset between curves 530 and 540.

Turning next to FIG. 5B, the graph 500B depicts a substantially linear relationship 580 between the wavelength shift 560 (in nanometers, nm) and the salinity 570 (in molarity, M) extracted by analyzing the shift of the lower envelope of the output depicted in FIG. 5A. Thus, by determining the wavelength shift between the output of a Fabry-Perot interferometer 300 in a known solution (e.g., pure water) and the output of the Fabry-Perot interferometer 300 in a saline solution, the optical spectral analyzer 320 may determine the salt concentration, or salinity, and temperature of the saline solution.

Figure 6A:
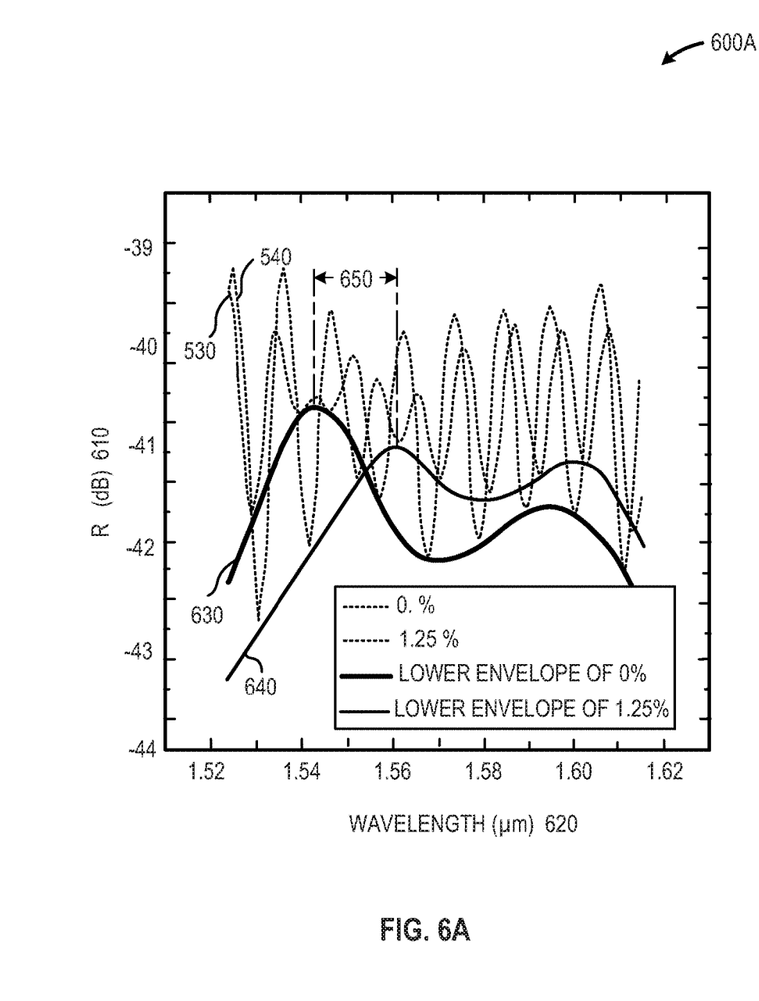
FIG. 6A is a graph in which a first curve represents the lower envelope of the optical output spectrum of the illustrative Fabry-Perot interferometer such as depicted in FIG. 3 when placed in pure water (i.e., 0% salt solution), and in which a second curve represents the lower envelope of the optical output spectrum of the illustrative Fabry-Perot interferometer such as depicted in FIG. 3 when placed in a 1.25% salt solution, in accordance with at least one embodiment described herein.
Figure 6B:
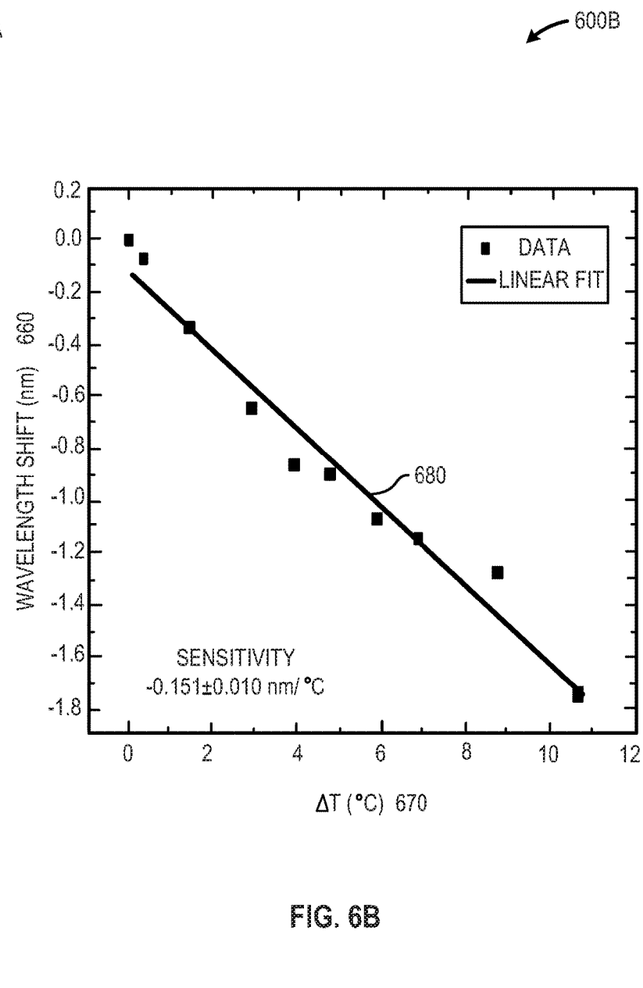
FIG. 6B is a graph that illustrates the temperature sensitivity of the illustrative Fabry-Perot interferometer, such as depicted in FIG. 3, as a function of wavelength shift, in accordance with at least one embodiment described herein.

FIG. 6A is a graph 600A in which curve 630 represents the lower envelope of the optical output spectrum 530 of the illustrative Fabry-Perot interferometer 300 such as depicted in FIG. 3 when placed in pure water (i.e., 0% salt solution), and in which curve 640 represents the lower envelope of the optical output spectrum 540 of the illustrative Fabry-Perot interferometer 300 such as depicted in FIG. 3 when placed in a 1.25% salt solution, in accordance with at least one embodiment described herein. FIG. 6B is a graph 600B that illustrates the temperature sensitivity of the illustrative Fabry-Perot interferometer 300, such as depicted in FIG. 3, to wavelength shift attributable to changes in the refractive index of the liquid in which the Fabry-Perot interferometer 300 is placed, in accordance with at least one embodiment described herein.

Referring first to FIG. 6A, graph 600A depicts the relative signal strength 610 (in decibels, dB) of the illustrative Fabry-Perot interferometer 300 as a function of output optical signal wavelength 620 (in micrometers, μm). Curve 530 represents the signal strength of the illustrative Fabry-Perot interferometer 300 when placed in pure water (i.e., a 0% salt solution). Curve 630 depicts the lower envelope of curve 530. Curve 540 represents the signal strength of the illustrative Fabry-Perot interferometer 300 when placed in a 1.25% saline solution. Curve 640 depicts the lower envelope of curve 540. The shift or offset 650 between lower envelope curve 630 and lower envelope curve 640 may provides an indication of the salinity and temperature shifts of the saline solution.

Turning next to FIG. 6B, the graph 600B depicts the substantially linear relationship 680 between the wavelength shift 660 (in nanometers, nm) and the temperature 670 (in degrees Centigrade, ° C.). Thus, by determining the wavelength shift between the output of a Fabry-Perot interferometer 300 in a solution (e.g., pure water) at a known temperature and the output of the Fabry-Perot interferometer 300 in a saline solution at an unknown temperature, the optical spectral analyzer 320 may determine the temperature of the saline solution.

Figure 7:
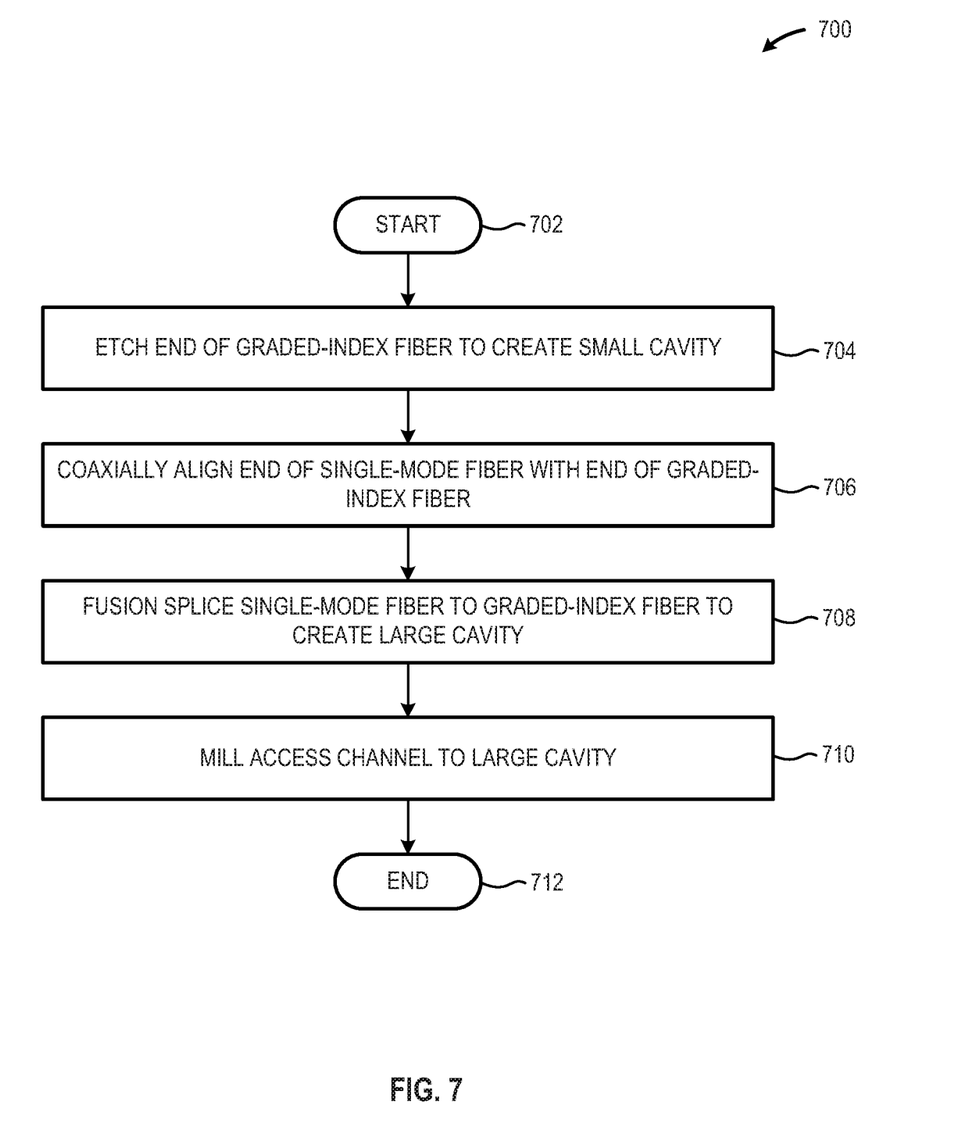
FIG. 7 is a flow diagram of an illustrative Fabry-Perot interferometer fabrication method, in accordance with at least one embodiment described herein.

FIG. 7 is a flow diagram of an illustrative Fabry-Perot interferometer fabrication method 700, in accordance with at least one embodiment described herein. A salinity and temperature sensor 210 may include a first, reference, Fabry-Perot interferometer 100A and a second, sensor or measurement, Fabry-Perot interferometer 100B. The first Fabry-Perot interferometer and the second Fabry-Perot interferometer may be fabricated using similar methods. In embodiments, the first Fabry-Perot interferometer 100A may include an open or a sealed large cavity 140. In embodiments, the first Fabry-Perot interferometer 100A may include a sealed large cavity 140 that is at least partially filled with a reference solution having one or more known parameters. In embodiments, one or more access channels 150 may be provide access to the large cavity 140 in the second Fabry-Perot interferometer 100B. The method 700 commences at 702.

At 704, material is removed from an end of a graded-index fiber 120 to form a relatively small cavity 130 in, on, about, or across at least a portion of the end of the graded-index fiber 120. In embodiments, the relatively small cavity 130 may be formed using any currently available and/or future developed material removal system or method. In at least some embodiments, the material may be removed from the end of the graded-index fiber 120 using a hydrofluoric acid gel.

At 706, a longitudinal axis 112 extending from an end of a single-mode fiber 110 is coaxially aligned with a longitudinal axis 122 extending from the relatively small cavity formed on the end of the graded-index fiber 120.

At 708, the end of the single-mode fiber 110 is fusion spliced to the end of the graded-index fiber 120 that includes the relatively small cavity 130. The fusion splicing process creates a relatively large cavity 140. At least a portion of the end of the single-mode fiber 110 provides a first reflective/transmissive surface in the relatively large cavity 140. At least a portion of the end of the graded-index fiber 120 provides a second reflective/transmissive surface in the relatively large cavity 140. In embodiments, the first reflective/transmissive surface may have a reflectivity of between about 0.1% and 15%. For example, the first reflective/transmissive surface may have a reflectivity of about 5%. In embodiments, the second reflective/transmissive surface may have a reflectivity of between about 0.1% and 15%. For example, the second reflective/transmissive surface may have a reflectivity of about 5%.

At 710, one or more access channels 150 may be formed in the wall of the relatively large cavity 140. In embodiments, the access channels 150 may fluidly couple the relatively large cavity 140 to the external environment about the Fabry-Perot interferometer. In embodiments, the access channels 150 may be formed using any currently available and/or future developed material removal systems or methods. For example, the one or more access channels 150 may be formed using a focused-ion beam. The method 700 concludes at 712.

Figure 8:
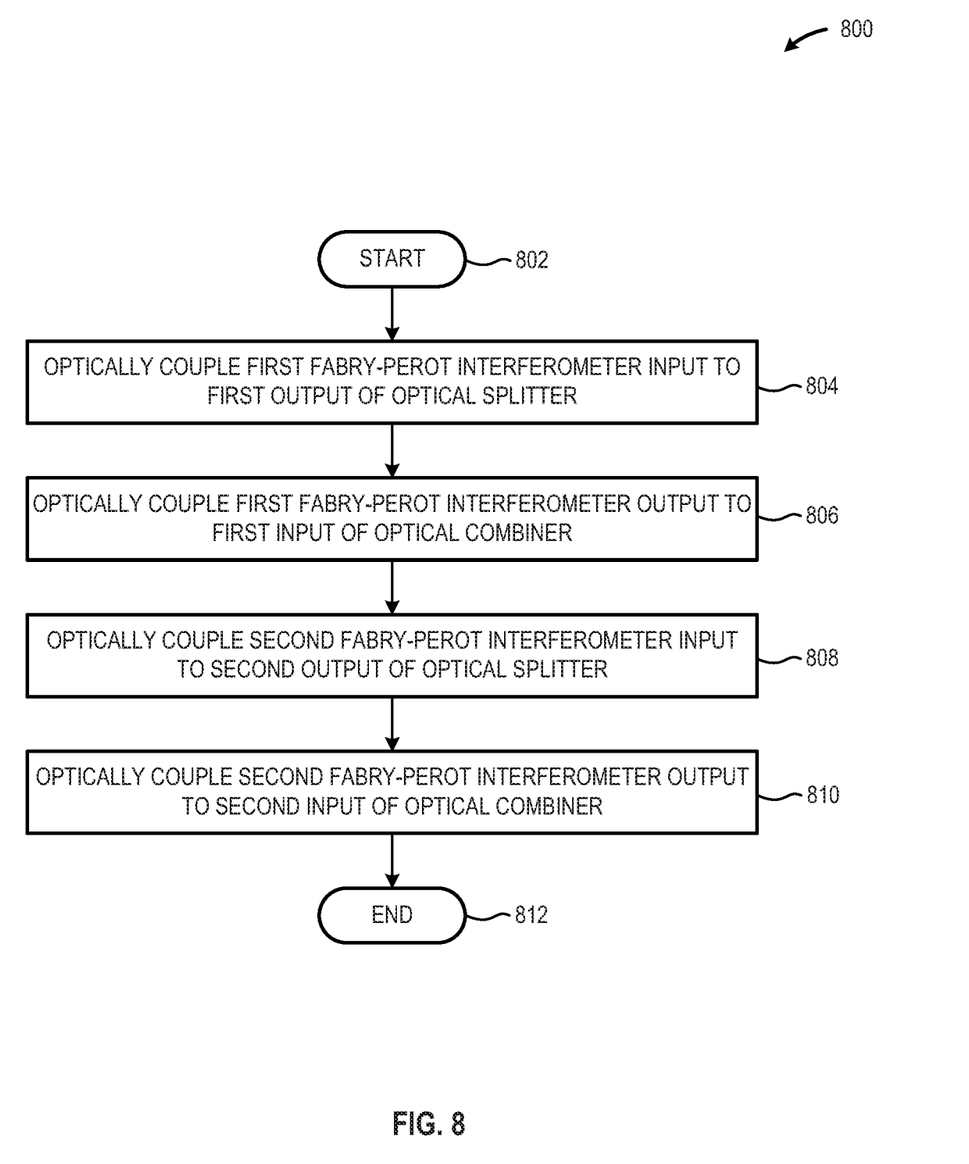
FIG. 8 is a flow diagram of an illustrative salinity and temperature sensor fabrication method, in accordance with at least one embodiment described herein.

FIG. 8 is a flow diagram of an illustrative salinity and temperature sensor 210 fabrication method 800, in accordance with at least one embodiment described herein. In embodiments, the salinity and temperature sensor 210 includes an optical signal splitter 230 to provide a broadband optical signal 222 to a first Fabry-Perot interferometer 100A and to a second Fabry-Perot interferometer 100B. The salinity and temperature sensor 210 also includes a signal combiner 240 to receive the optical interference signals 232A and 232B from the first Fabry-Perot interferometer 100A and the second Fabry-Perot interferometer. The method 800 commences at 802.

At 804, an input port of the first Fabry-Perot interferometer 100A is optically coupled to a first output of the optical signal splitter 230. The optical signal splitter 230 provides a broadband optical signal 222A to the first Fabry-Perot interferometer 100A.

At 806, an output port of the first Fabry-Perot interferometer 100A is optically coupled to a first input of an optical signal combiner 240. The optical signal combiner 240 receives a first optical output signal 232A that includes information and/or data representative of an interference pattern generated by the first Fabry-Perot interferometer 100A.

At 808, an input port of the second Fabry-Perot interferometer 100B is optically coupled to a second output port of the optical signal splitter 230. The optical signal splitter 230 provides a second broadband optical signal 222B to the second Fabry-Perot interferometer 100B.

At 810, an output port of the second Fabry-Perot interferometer 100B is optically coupled to a second input port of the optical signal combiner 240. The optical signal combiner 240 receives a second optical output signal 232B that includes information and/or data representative of an interference pattern generated by the second Fabry-Perot interferometer 100B. The optical signal combiner 240 provides the combined optical output signal 250 at an output port coupleable to an optical spectral analyzer 320. The method 800 concludes at 812.

Figure 9:
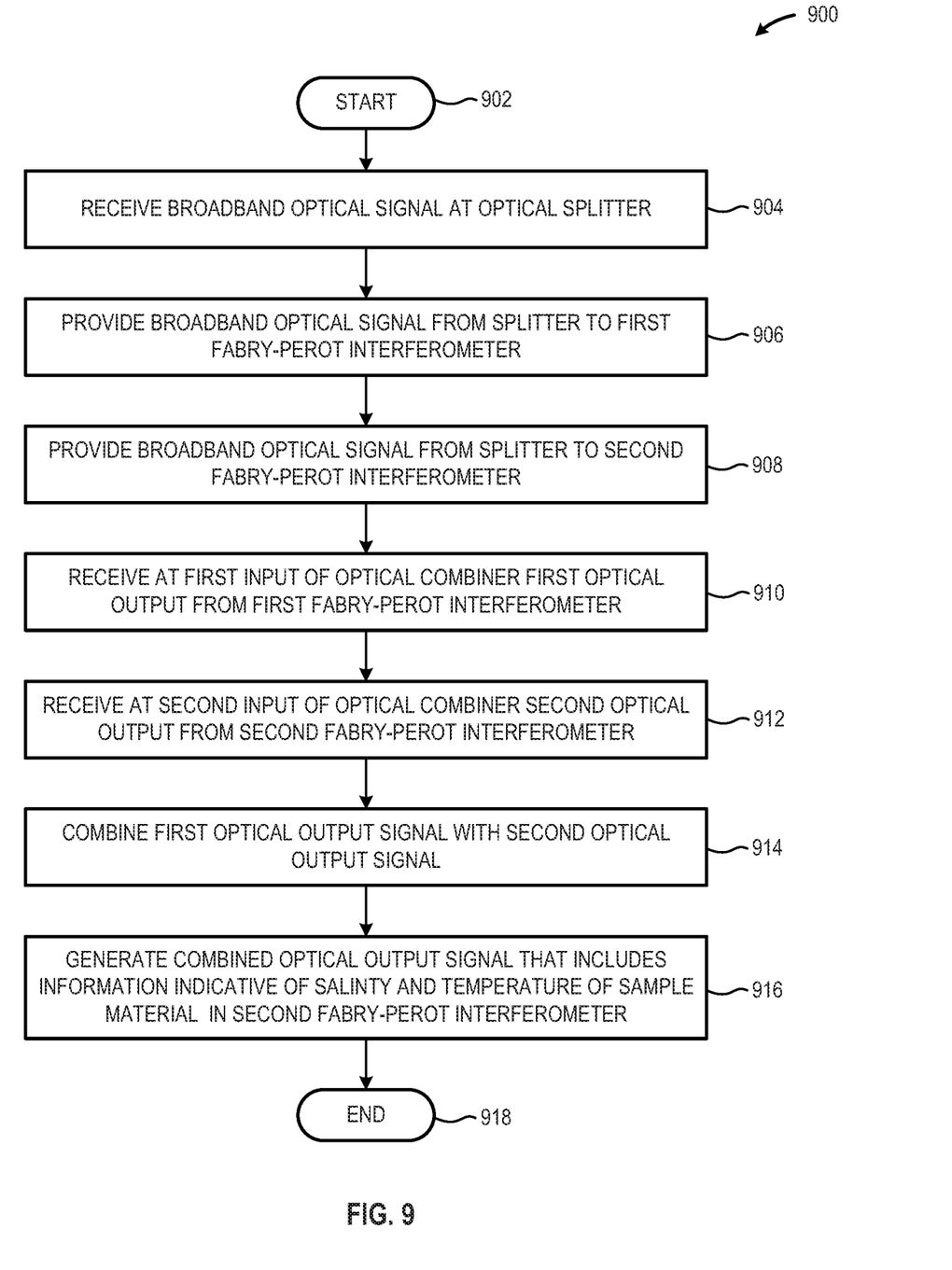
FIG. 9 is a flow diagram of an illustrative salinity and temperature measurement method that uses one or more fiber salinity and temperature sensors coupled to a broadband optical source and an optical spectral analyzer to determine values representative of the salinity and temperature in proximity to each of the one or more fiber salinity and temperature sensors, in accordance with at least one embodiment described herein.

FIG. 9 is a flow diagram of an illustrative salinity and temperature measurement method 900 that uses one or more fiber salinity and temperature sensors 210 coupled to an optical source 310 and an optical spectral analyzer 320 to determine values representative of the salinity and temperature in proximity to each of the one or more fiber salinity and temperature sensors 210, in accordance with at least one embodiment described herein. Although FIG. 9 discloses a salinity and temperature measurement method 900 with respect to a single salinity and temperature sensor 210, the method 900 may be extended to cover any number of salinity and temperature sensors 210 arranged in a linear, planar, or three-dimensional array. The method 900 commences at 902.

At 904, an optical signal splitter 230 receives, via an optical fiber 220 coupled to an input port, a broadband optical signal 222 produced by an optical source 310. In embodiments, the broadband optical signal 222 may include any number and/or combination of optical signals at one or more frequencies and/or in one or more frequency bands. For example, in a network containing "n" salinity and temperature sensors 210, the broadband optical signal 222 received by the optical signal splitter may include up to "n" frequencies and/or "n" frequency bands that includes one or more frequencies.

At 906, the optical signal splitter 230 provides, via a single-mode fiber 110A, a first broadband optical signal 222A to an input port of a first, reference, Fabry-Perot interferometer 100A. In embodiments, the first broadband optical signal 222A may include all of the one or more frequencies/frequency bands included in the broadband optical signal 222. In other embodiments, the first broadband optical signal 222A may include only a portion of the one or more frequencies/frequency bands included in the broadband optical signal 222.

At 908, the optical signal splitter 230 provides, via a single-mode fiber 110B, a second broadband optical signal 222B to an input port of a second, measurement or sensor, Fabry-Perot interferometer 100B. In embodiments, the second broadband optical signal 222B may include all of the one or more frequencies/frequency bands included in the broadband optical signal 222 to the second Fabry-Perot interferometer 100B. In other embodiments, the second broadband optical signal 222B may include only a portion of the one or more frequencies/frequency bands included in the broadband optical signal 222.

At 910, the first Fabry-Perot interferometer 100A provides, via a graded-index fiber 120A, a first optical output signal 232A to a first input port of an optical combiner 240. The first optical output signal 232A includes information and/or data representative of an optical interference pattern produced by the first Fabry-Perot interferometer 100A. The interference pattern produced by the first Fabry-Perot interferometer 100A is influenced by the refractive index of the reference material 212 in the large cavity 150 of the first Fabry-Perot interferometer 100A. In some implementations, the large cavity 150 of the first Fabry-Perot interferometer 100A may contain a reference material having a known refractive index. In some implementations, the large cavity 150 of the first Fabry-Perot interferometer 100A may be hermetically sealed (i.e., may not contain access channels 150) from the external environment about the salinity and temperature sensor 210.

At 912, the second Fabry-Perot interferometer 100B provides, via a graded-index fiber 120B, a second optical output signal 232B to a second input port of the optical combiner 240. The second optical output signal 232B includes information and/or data representative of an optical interference pattern produced by the second Fabry-Perot interferometer 100B. The interference pattern produced by the second Fabry-Perot interferometer 100B is influenced by the refractive index of the sample material 214 introduced to, or flowing through, the large cavity 140 in the second Fabry-Perot interferometer 100B. In some implementations, the large cavity 140 in the second Fabry-Perot interferometer 100B a liquid having a quantifiably variable refractive index may flow through the large cavity 140 of the second Fabry-Perot interferometer 100B. For example, a saline solution in which the refractive index of the solution varies with salt concentration may be introduced to or flow through the large cavity 140 in the second Fabry-Perot interferometer 100B. In embodiments, the interference pattern produced by the second Fabry-Perot interferometer 100B will differ from the interference pattern produced by the first Fabry-Perot interferometer 100A.

At 914, the optical combiner 240 combines all or a portion of the first optical output signal 232A with all or a portion of the second optical output signal 232B.

At 916, the optical combiner 240 provides, at an output port, a combined optical signal 250 that includes data and/or information representative of at least a portion of the first interference pattern produced by the first Fabry-Perot interferometer 100A and at least a portion of the second interference pattern produced by the second Fabry-Perot interferometer 100B. The difference (or shift) between the first interference pattern and the second interference pattern may provide information and/or data indicative of one or more parameters associated with the sample material 214 disposed in or flowing through the large cavity 140 of the second Fabry-Perot interferometer 100B. In embodiments, the combined optical signal 260 may be provided to an optical signal analyzer 320 to determine the shift or difference between the first interference pattern and the second interference pattern and to determine one or more parameters (e.g., salinity and temperature) associated with the sample material 214 disposed in or flowing through the large cavity 140 of the second Fabry-Perot interferometer 100B. The method 900 concludes at 918.

While FIGS. 7 through 9 illustrate various operations according to one or more embodiments, it is to be understood that not all of the operations depicted in FIGS. 7 through 9 are necessary for other embodiments. Indeed, it is fully contemplated herein that in other embodiments of the present discolsure, the operations depicted in FIGS. 7 through 9, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

What is claimed:

1. A salinity and temperature measurement system comprising:
   an optical source;
   an optical spectral analyzer; and
   a fiber-optic salinity and temperature sensor, comprising:
      a first Fabry-Perot interferometer comprising a reference cell formed between a first single-mode optical fiber and a coaxially aligned first graded-index fiber;
      a second Fabry-Perot interferometer that includes a measurement cell formed between a second single-mode optical fiber and a coaxially aligned second graded-index fiber;
      an optical splitter having an input port optically coupled to the optical source, a first output port optically coupled to the first single-mode optical fiber and a second output port optically coupled to the second single-mode optical fiber; and
      an optical combiner having a first input port optically coupled to the first graded-index fiber, a second input port optically coupled to the second graded-index fiber, and an output port optically coupled to the optical spectral analyzer.

2. The system of claim 1 wherein the first Fabry-Perot interferometer comprises:
   a first cavity disposed between the first single-mode optical fiber and the first graded-index fiber;
      wherein an end of the first single-mode optical fiber opposite the first optical coupler provides at least a portion of the first reflective surface of the first Fabry-Perot interferometer;
      wherein the first graded-index fiber provides at least a portion of a second reflective surface of the first Fabry-Perot interferometer.

3. The system of claim 2 wherein the second Fabry-Perot interferometer comprises:
   a second cavity disposed between the second single-mode optical fiber and the second graded-index fiber;
      wherein an end of the second single-mode optical fiber opposite the first optical coupler provides at least a portion of the first reflective surface of the second Fabry-Perot interferometer;
      wherein the second graded-index fiber provides at least a portion of a second reflective surface of the second Fabry-Perot interferometer.

4. The system of claim 3 wherein the second cavity comprises a cavity having an axial length of from 50 micrometers (μm) to 200 μm.

5. The system of claim 1 wherein the optical source comprises a source having an electromagnetic output wavelength of about 1550 nanometers (nm).

6. A method for fabricating a fiber-optic salinity and temperature sensor, comprising:
   optically coupling an input port of a first Fabry-Perot interferometer to a first output port of an optical splitter;
   optically coupling an output port of the first Fabry-Perot interferometer to a first input port of an optical combiner;
   optically coupling an input port of a second Fabry-Perot interferometer to a second output port of the optical splitter;
   optically coupling an output port of the second Fabry-Perot interferometer to a second input port of the optical combiner;
   forming each of the first Fabry-Perot interferometer and the second Fabry-Perot interferometer by:
      etching an end of a graded-index fiber to create a small cavity on the end of the graded-index fiber, wherein the small cavity forms at least a portion of a first surface of a chamber in the respective Fabry-Perot interferometer;
      coaxially aligning an end of a single-mode fiber with the small cavity formed on the end of the graded-index fiber, wherein the end of the single-mode fiber forms a second reflective surface of the chamber in the respective Fabry-Perot interferometer;
      fusion splicing the end of the single-mode fiber to the small cavity formed on the end of the graded-index fiber to form a large cavity in the respective Fabry-Perot interferometer; and
      milling an access channel to the large cavity in the second Fabry-Perot interferometer.

7. The method of claim 6, further comprising:
   optically coupling an optical source to an input port of the optical splitter.

8. The method of claim 7 wherein optically coupling the broadband optical source to the input port of the optical splitter comprises:
   optically coupling a broadband optical source having a spectral peak at about 1550 nanometers (nm) to the input port of the optical splitter.

9. The method of claim 7, further comprising:
   optically coupling a photoreceiver to an output port of the optical combiner.

10. The method of claim 9 wherein optically coupling the photoreceiver to the output port of the optical combiner comprises:
    optically coupling an optical spectral analyzer to the output port of the optical combiner.

11. The method of claim 6 wherein, for each of the first Fabry-Perot interferometer and the second Fabry-Perot interferometer, etching the end of graded-index fiber to create the small cavity on the end of the graded-index fiber comprises:
    etching the end of the graded-index fiber with a hydrofluoric acid gel to create the small cavity on the end of the graded-index fiber.

* * * * *